United States Patent [19]
Devos

[11] Patent Number: 4,919,920
[45] Date of Patent: Apr. 24, 1990

[54] METHOD OF HARDENING AND STRENGTHENING KERATIN AND COMPOSITION

[76] Inventor: John B. Devos, 117 Lake St., Libertyville, Ill. 60048

[21] Appl. No.: 323,974

[22] Filed: Mar. 15, 1989

[51] Int. Cl.$^5$ .................. A61K 7/04; A61K 33/16
[52] U.S. Cl. .................... 424/61; 424/673; 424/676; 514/769
[58] Field of Search .............. 424/673, 676, 61; 514/769

[56] References Cited

U.S. PATENT DOCUMENTS

| | | | |
|---|---|---|---|
| 2,261,623 | 11/1941 | Hucks | 167/85 |
| 2,887,116 | 5/1959 | Wooding | 132/73 |
| 3,034,965 | 5/1962 | Drake et al. | 167/85 |
| 3,034,966 | 5/1962 | Williams | 167/85 |
| 3,234,097 | 2/1966 | Loughran et al. | 167/85 |
| 3,257,280 | 6/1966 | Richter | 167/85 |
| 3,326,762 | 6/1967 | Joullie et al. | 167/85 |
| 3,725,525 | 4/1973 | Joos | 424/61 |
| 3,989,817 | 11/1976 | Mayer | 424/61 |
| 4,073,887 | 2/1978 | McLean | 242/147 |
| 4,631,186 | 12/1986 | Brown | 424/61 |

OTHER PUBLICATIONS

Achten, G., "The Normal Nail", *Amer. Perf. Cosmet.*, 79 23 (1984).
Louffer, P., "Brittle Nails", *Amer. Perf. Cosmet.*, 81 71 (1966).
Tronnier, H., "Diseases and Cosmetic Treatments of the Nails", *Cosmet. Toilet.*, 103, 67 (1988).
McCarty, L. F., "Beauty Answers", *Vogue*, 179, No. 2, 176 (1989).

*Primary Examiner*—Henry F. Epstein
*Assistant Examiner*—Susan S. Rucker
*Attorney, Agent, or Firm*—Olson & Hierl

[57] ABSTRACT

The present invention discloses a method and aqueous composition for hardening and strengthening the keratinized appendages of mammals, and the nail keratin of humans, in particular. The aqueous keratin hardening and strengthening composition includes an effective amount of fluoride ion. The topical application of the fluoride ion is effected from an aqueous cosmetic vehicle capable of maintaining moist contact with the keratin for a sufficient period of time in the method practiced. Auxiliary keratin-strengthening agents are also disclosed.

35 Claims, No Drawings

METHOD OF HARDENING AND STRENGTHENING KERATIN AND COMPOSITION

TECHNICAL FIELD

This invention relates to improvements in beauty aids for increasing the hardness and strength of keratinized appendages of mammals. In particular, the invention relates to a topical composition containing an effective amount of a fluoride ion and method therefor.

BACKGROUND OF THE INVENTION

Substantially solid structures occur in living mammals, such as vertebrate animals and humans, as keratinized appendages to the skin. These keratinized appendages include the nails of humans, and the horns, hoofs, and claws of animals. In the living mammal, such keratinized appendages are subjected to countless traumas from the environment to which they are exposed during everyday movements.

In humans, the hardness and strength of the nails, which includes fingernails and toenails, is particularly important not only for the beauty of their appearance, but for the well-being of the individual. Embrittlement of the nails is normally associated with aging. However, various activities expose the nails to a number of materials which also adversely affect the nail's physico-mechanical condition.

For example, occupational exposure to extensive or constant wetting of the hands with soaps, detergents, solvents, chemical hair waving and coloring lotions, and insults from deliberate cosmetic applications, such as manicuring, or any like products can lead to drying, brittleness, cracking, laminating, splitting, ridging and similar damage. Additionally, certain diseases of widely different causes and symptoms can also lead to nail embrittlement or associated disfigurement owing to weakening of nail hardness and strength.

It is sometimes desirable to enhance and improve the beauty of such keratinized appendages such as the horns, hoofs and claws of living animals for show. The appearance of fingernails and toenails of humans, in particular, are frequently enhanced with decorative nail-care cosmetics, such as nail polishes, nail polish removers, nail polish bases, alkaline cuticle removers and the like. Overuse of these products can alter the nail keratin causing it to weaken, soften, split and break.

Nail-care cosmetics and nail polishes in particular, contain organic solvents that can undesirably defat or degrease the nail, i.e., remove the natural cementing substance of the nail, and so promote drying embrittlement. Past attempts to recondition the nails have included topically regreasing them by rubbing with oils or lipids. But the nail has to be degreased again in order for a new layer of polish to adhere.

In the past, remedial approaches have included applying solutions of formaldehyde or formaldehyde donors, sodium iodide, or astringents in an attempt to chemically harden the nail keratin. However, many of these chemicals can irritate the surrounding skin tissue and lead to allergies. Moreover, iodides can discolor the nails. Alternatively, the nails have been physically strengthened by applying some temporary artificial protective coating, such as a network of nylon fibers, polymers, artificial fingernails, and the like.

Numerous nail-hardening or nail-strengthening products have been made and marketed with varying degrees of success. However, many of these products do not simultaneously harden and strengthen the nail keratin and many contain organic solvents which can degrease the nails. For example, "nail-mending" kits typically consist of a non-woven cloth for application to the nail and require a solvent-based adhesive and solvent-based topcoat for such application.

There is a long-recognized need for a solvent-free nail-care cosmetic capable of simultaneously hardening and strengthening nail keratin without degreasing the nail of its natural cementum and without irritating the surrounding skin tissues. The present invention provides such a product and a method for applying the product to the keratinous surface.

SUMMARY OF THE INVENTION

The present invention relates to the use of an effective amount of fluoride ion in a cosmetically acceptable form for simultaneously hardening and strengthening the keratinized appendages of mammals, especially humans. In particular, application of fluoride ion is effected by means of an aqueous, organic solvent-free cosmetic vehicle capable of maintaining moist contact with the surface of keratinized appendages, such as the nails of humans, and the horns, hoofs and claws of animals.

An aqueous fluoride ion-containing keratin hardening and strengthening composition is advantageously applied topically by the method of the invention. More particularly, the source of effective fluoride ion is from at least one fluoride compound dissolved in an aqueous cosmetic vehicle having a physiologically acceptable pH. Preferably, the composition includes an auxiliary keratin-strengthening agent which is a reconditioner and has sufficient viscosity to keep the composition from dripping from the keratinous surface to which it is applied.

In the method of this invention, a sufficient amount of keratin hardening and strengthening composition is topically applied to contact and coat all exposed keratinous surfaces of the body of the appendage. The applied composition is maintained in moist contact for a sufficient hardening and strengthening period of at least about 1 minute, preferably at least about 5 minutes. The composition is then removed. In the case of fingernails and the toenails of humans, the composition is preferably applied to coat the nail body including the exposed dorsal nail zone, the cuticle, and to the anterior extremity (free edge or nail tip). Repeat application of a keratin hardening and strengthening composition, preferably at least once daily, can be performed until the desired hardening and strengthening is achieved.

One surprising aspect of the composition of the invention is that fluoride-ion is effective as a primary agent for simultaneously hardening and strengthening keratin. Fluoride ion is effective in an amount which is non-toxic to mammals and physiologically tolerable by the tissue of the keratin appendage to which the composition is applied. Fluoride ion from inorganic fluoride compounds, such as water-soluble fluoride salts and water-soluble complex fluoride salts, used alone or in combination, is particularly preferred. Preferably, at least about 500 parts per million fluoride ion is present in the composition.

In another surprising aspect of the composition of the invention, certain reconditioners are useful auxiliary keratin-strengthening agents in combination with fluoride ion based keratin hardening and strengthening. The term "reconditioner" or "reconditioners" as used herein denotes substantially hygroscopic cosmetic emollient materials capable of effecting either rehydration or of regreasing or both of the nail keratin. Reconditioning preserves or restores smooth characteristics normally associated with the natural cementum of nail keratin and its pliable strength. Preferably, the reconditioners are selected from the group consisting of cosmetically-acceptable lipids and polyols, used individually or in combination.

In a particularly preferred composition, effective fluoride ion is obtained from at least one fluoride compound including a cation selected from the group consisting of aluminum, ammonium, sodium, potassium and tin. The auxiliary keratin strengthening agent is preferably a phospholipid or a polyhydric aliphatic alcohol having at least three carbon atoms in the aliphatic chain and at least two hydroxyl groups, or, more preferably, a combination of both.

For purposes of keeping the composition from dripping from the keratinous surface and for maintaining the composition in moist contact with that surface, a water-swellable thickening agent is preferably included. Additionally, cosmetically-desirable adjuvants for soothing the skin tissues surrounding the keratinous appendage and auxiliary cosmetic materials used for their generally known purposes can be included in the composition.

The advantage of the present invention is that desirable hardening and strengthening of nail keratin, in particular, can be achieved in a controlled, cosmetically-acceptable manner. Another benefit is that the aqueous keratin hardening and strengthening composition is free of degreasing solvents.

Another benefit is that a composition embodying the principles of this invention is easy to apply and easy to remove.

Another advantage is that the method and composition of this invention can be practiced as part of a nail-care regimen without interfering with the use of other nail-care cosmetics, such as nail polish.

A particular benefit is that the method and composition can be selectively practiced on the exposed tips of the nails and on the exposed cuticles by wearers of nail polish as part of their nail-care regimen without having to remove the polish.

Still further benefits will be apparent to those skilled in the art from the description, examples and claims which follow.

DETAILED DESCRIPTION OF THE INVENTION

This invention relates to compositions and methods for improving and enhancing the physico-mechanical properties of keratinized appendages of mammals. The present invention is based in part on the finding that fluoride ion can be used to simultaneously harden and strengthen the keratin of the nails of humans. Additionally, the present invention is based on the finding that the hardening and strengthening effect of fluoride ion can be supplemented by combining it with reconditioning amounts of auxiliary keratin-strengthening agents, such as lipids and polyols.

The term "keratin" refers to the substantially solid sulfur-containing protein that makes up the noncollagenous keratinized appendages of living vertebrate mammals. The term "keratin-hardening" as used herein refers to increasing the physical resistance of the surface of a keratinized appendage to deformation or damage from externally applied forces, such as from scratching, denting, hitting, pressure and the like. The term "keratin-strengthening" as used herein refers to increasing the physical strength of the flexion of a keratinized appendage against breaking on being flexed or bent. The term "keratin hardening and strengthening" means each of the foregoing individual beneficial characteristics are achieved simultaneously. The term "auxiliary keratin-strengthening" refers to enhancing the pliability of the keratin by retaining its natural non-brittle, elasticity, and resiliency. With reference to human nails, "auxiliary keratin-strengthening" also includes the natural smooth character of the keratin to which the natural cementing substance in the nail contributes.

For purposes of illustrating the invention, but not for limiting it, the hardening and strengthening of human nail keratin by fluoride ion will be discussed.

The nails of humans are a modification of the horny epidermal cells and are composed of what is known as "hard" keratin. The cells have a laminated arrangement similar to those composing the epidermis and form a flattened elastic structure having a horny texture on the terminal phalanges. Normal nails grow approximately three to four millimeters per month unless inhibited by disease.

The chemical composition of the normal nail resembles that of the upper layer of the epidermis, except that they contain a somewhat larger proportion of sulfur. Nail keratin is rich in sulfur, primarily in the form of cystine, and to a lesser extent in the form of methionine. Cystine contents of about 8 to about 12 percent of the nail weight and less than 1 percent methionine have been reported in the literature.

Keratin represents the main substance of the nail generally as an insoluble scleroprotein. Its protein is generally surrounded by cementing mucopolysaccharides. The normal nail has been reported to contain more than about 14 percent water, as well as lipids in the form of cholesterol (sometimes called cholesterin). Additionally, calcium, phosphorous and a number of metals, including zinc, magnesium, copper, iron and manganese have been reportedly found in nails.

A discussion of the chemical and physical characteristics of nails and of some prior remedial measures against embrittlement can be found in the cosmetic literature. See, for example, Lauffer, "Brittle Nails," *Amer. Perf. Cosmet.*, 81, 71-72 (1966) and in Achten, "The Normal Nail," *Amer. Perf. Cosmet.*. 79, 23-26 (1964), the relevant disclosures of which are incorporated herein by reference.

The lipids present in nail keratin, as in other horny epidermal layers, can occur as free lipids or as part of the keratin molecule and appear to preserve the normal pliability of the keratin structure by some emollient action. In the case of normal skin, for example, surface lipids are believed to play a physical role of lubrication and protection as well as maintaining the current degree of hydration in the stratum corneum. Lipids are known to be important in maintaining the linear polymerization of keratin molecules in soft keratin and the removal of these lipids can change the appearance of the keratin from fibrillar to granular. It is believed that a similar situation may exist in the hard keratin of nails. Consequently, a common external cause of nail damage is attributed to the extraction of small amounts of lipids normally present in the nail keratin by solvents, detergents and the like.

In the present invention, fluoride ion has been found surprisingly effective as a primary agent for hardening and strengthening keratin, especially nail keratin. More particularly, fluoride ion from water-soluble fluoride salts, and water-soluble complex fluoride salts, used alone or in combination can be applied topically to nail keratin by means of an aqueous cosmetic composition.

Nail keratin increases in hardness and strength with each application of fluoride ion-containing composition, without discoloration of nail protein or irritation of the tissues of the skin surrounding the body of the nail, when the method of this invention is practiced.

Preferably, an effective amount of at least about 500 parts per million fluoride ion or more is present in the composition. However, it is recognized that lesser or greater amounts of fluoride ion will also harden and strengthen nail keratin but will differ in the speed with which the hardening is achieved. Thus, small amounts of fluoride ion will achieve the hardening and strengthening effect slowly, while greater amounts of fluoride ion can decrease the time required for hardening and strengthening. However, it has also been found that hardening the nail keratin too quickly can also cause brittleness which would be undesirable.

The selection of the actual effective amount of fluoride ion in the composition can be readily determined or controlled in part by the water-solubility of the compound which constitutes the source of the fluoride ion. Another determining factor is that the effective amount of fluoride ion present be substantially non-toxic to the subject to which the composition will be applied and substantially physiologically tolerable by (i.e., non-irritating to) the tissues of the skin surrounding the nail. Other considerations are, of course, cost and availability of the fluoride compounds.

Preferably, the active fluoride compound which constitutes the source of fluoride ion includes a cation that forms a substantially color-free compound. Preferably such fluoride compounds include a cation selected from the group consisting of aluminum, ammonium, sodium, potassium and tin. Exemplary useful fluoride compounds include aluminum fluoride, sodium fluoride, potassium fluoride, stannous fluoride, ammonium hexafluorophosphate, sodium monofluorophosphate, stannous fluorozirconate, stannous chlorofluoride and stannous monofluorophosphate, used alone or in combination. Sodium fluoride, sodium monofluorophosphate and stannous fluoride are particularly preferred owing their commercial availability in relatively pure pharmaceutical grades.

Finding fluoride ion to be an effective primary agent for simultaneously hardening and strengthening nail keratin was not only surprising but unexpected. In the past, iodide ion had been used as a chemical crosslinking agent to harden fingernails by painting the nails with a solution of sodium iodide. Iodide salts have also been used in relatively minor amounts as promoters or catalysts in water-in-oil emulsions where walnut oil is the active primary agent for hardening nails as described in U.S. Pat. No. 3,989,817. However, where the primary active ingredient contains unsaturated components, such as walnut oil, interaction between the iodide ion can occur. Moreover, compositions including iodide ion tend to be unstable and can release iodine which discolors the nail protein.

Quaternary ammonium salts of bromide or chloride have been used as cuticle softeners, primarily for their bactericidal effects and for the smoothness given the keratin by the affinity of the quaternary for protein. Bromide ions, otherwise, are not generally cosmetically useful and can cause allergic reactions, and chloride ions are known to play a role in the swelling behavior of keratins. Thus, except for the limited utility of iodide ion, none of the other halide ions have been known in the past to have any hardening or strengthening effect on keratin.

Compositions of this invention for hardening and strengthening of nail keratin by fluoride ion can be practiced by preparing an aqueous fluoride ion-containing composition having a physiologically acceptable pH. The pH is preferably about pH 3.5 and 8, more preferably about 4 to about 7, most preferably about pH 5 to about 6. The pH of the composition can be adjusted, if necessary, with acids or bases used for this purpose in cosmetics and pharmaceuticals. Suitable acids preferably include phosphoric acid, citric acid, tartaric acid, lactic acid and the like. Suitable bases include sodium hydroxide, potassium hydroxide, sodium carbonate, and lower alkyl organic amines and hydroxy amines in which the alkyl group contains from 1 to 6 carbon atoms.

The method of this invention can be practiced by applying a keratin hardening and strengthening composition topically to the body of the nail keratin using an amount sufficient to substantially contact and coat all exposed keratinized surfaces. The term "coat" means that a relatively thick layer of at least about 1 millimeter or more (at least about 0.04 inches or more) of the composition is applied. To keep or prevent the composition from dripping from the surface and to maintain the applied composition in substantially moist contact with the surface the composition preferably includes a thickening agent.

The beneficial keratin hardening and strengthening effect of fluoride ion is enhanced and achieved more quickly by maintaining the hardening and strengthening composition in a moist state in contact with the nail keratin and for as long as is reasonably possible. A sufficient hardening and strengthening period of between at least about one minute to about 30 minutes is useful for each application. As a practical matter, an effective period of between at least about 5 minutes to about 15 minutes was found sufficient and desirable. For example, a daily application period of at least about 5 minutes with a composition containing about 2 weight percent sodium fluoride, was found effective and preferred.

An aqueous fluoride-ion containing composition according to the method of this invention, is preferably prepared in the form of a non-runny syrup or gel. More preferably, the rheology of the composition is thixotropic. A thixotropic composition or gel preferably provides a relatively thick coating on the keratin surface and remains moist throughout the contact time, and can be readily applied and removed.

In practicing the method of this invention, after a sufficient hardening and strengthening period, residual composition is removed from the nail. Excess composition, if any, can be removed by wiping with a tissue followed by washing the nails with water. Alternatively, the excess composition can be rinsed off with water directly.

By applying the keratin hardening and strengthening composition, preferably at least once daily, the desired hardness and strength of the nail keratin can be achieved and controlled even as the nail grows. Moreover, the application of the keratin hardening and strengthening composition can be carried out even if nail polish is present, so long as the composition contacts some exposed portion of the nail keratin surface. Consequently, the invention can be practiced to harden and strengthen selective parts of the nail body. For example, the keratin hardening and strengthening composition can be applied only to the free edge of the nail, if desired, to harden and strengthen the nail tips. Alternatively, the composition can be applied only to the cuticle area of the nail once the initial desired level of hardness and strength of the body of the nail has been attained or if nail polish is present. Thus, a keratin hardening and strengthening composition and the method of this invention can be practiced as a user's sole normal nail-care regimen or in conjunction therewith.

It is well known, as discussed earlier, that the natural emollient components or natural "greases" present in the cementing substance of nail keratin are extracted and removed by solvent-based nail care cosmetics and by detergents, soaps and the like. Typically, prior attempts to recondition the nail relied on rubbing in oleaginous materials, oils, waxes and the like in an attempt to regrease the nails. However, the presence of such materials on the surface can interfere with the subsequent use of nail-care cosmetics. For example, an oily buildup can prevent nail polish film from properly adhering. Alternatively, a buildup of an occlusive coating can also interfere with the normal transpiration of moisture through the nail. This can result in too much water retention which in turn can cause softening and weakening.

Chemical hardening, while a desirable end in itself, does not normally restore the smooth characteristics associated with the natural protective cementum of the nail keratin which has been lost and which helps maintain its natural pliable state. Surprisingly, a fluoride ion-based keratin hardening and strengthening composition of this invention can achieve desirable smoothness by including auxiliary keratin-strengthening agents which are reconditioners as defined earlier. By effecting the application of the fluoride ion to the nail keratin from an aqueous cosmetic vehicle, particularly a vehicle including a thickening agent and relatively small reconditioning amounts of auxiliary keratin-strengthening agent, emollient reconditioning of the nail keratin is believed to also take place.

The term "relatively small amount" refers to an amount that represents no more than about 5 weight percent and preferably no more than about 3 weight percent of the composition. In a preferred embodiment, effective reconditioning was found with a combination of lipid and polyol at a weight ratio of about 1:1 to about 1:2, respectively.

For example, in a particularly preferred aqueous composition comprising about 2 weight percent sodium fluoride and a thickening agent, a combination of lipid and glycol present at a combined weight percent of about 1 to about 2 weight percent was judged an effective reconditioning amount of auxiliary keratin-strengthening agent. In this embodiment, the auxiliary keratin-strengthening agent was effective in an amount equivalent to or less than the amount of fluoride compound present.

The term "lipid" as used herein denotes fats and fat-like substances which are relatively insoluble in water and generally soluble in organic solvents and are related either actually or potentially to fatty acid esters, fatty alcohols, sterols, waxes and derivatives of each. Lipids are generally classed as neutral fats, phospholipids, cerebrosides, sterols, lipoproteins, structurally related carotenoids, vitamins A, D, E and K and the like. Phospholipids are particularly preferred.

The term "neutral fats" denotes the glyceryl esters and glyceryl ethers of long chain saturated or unsaturated fatty acids having at least about 12 carbons. The term "fats" includes the foregoing long chain fatty acids derived from or contained in an animal or vegetable fat or oil. The term "phospholipids" includes glycerol esters containing phosphoric acid, such as phosphoglycerides, such as lecithin, and phosphatides such as phosphatide-ethanolamine. As used herein, the term phospholipids includes lecithin and water-dispersible, water-soluble and alcohol-soluble derivatives of lecithin, such as acetylated lecithin, partially hydrolyzed lecithin, hydroxylated lecithin, hydrogenated lecithin and similarly modified lecithin and phospholipid complexes derived from lecithin. Lecithin is a particularly preferred lipid owing to its hydrophilic and hydrophobic properties.

The term "sterols" as used herein denotes cosmetically useful sterols derived from animal and vegetable fats. For example, cholesterol (also known as cholesterin), cholesterol esters preferably derived from lanolin, and derivatives thereof which are structurally similar to naturally occurring epidermal lipids, surface lipids and sebum of humans and animals. Vegetable sterols include phytosterol, ergosterol, sitosterol and stigmasterol.

The term "polyol," as used herein, denotes a polyhydric aliphatic alcohol having three or more carbon atoms in the aliphatic chain and two or more hydroxyl groups. Exemplary useful polyols include glycerol, propylene glycol, hexylene glycol, butylene glycol, and sugar alcohols having the general formula $CH_2OH(CHOH)_nCH_2OH$ where "n" may be from 2 to 5, such as sorbitol. Glycerol is particularly preferred.

The actual amount of auxiliary keratin-strengthening agent can be readily determined by persons skilled in the cosmetic art. Determining factors include the extent of emollient effect desired, the effect of the emollient ingredient on the viscosity of the composition or on its appearance, as well as cost and stability in solution.

Thickening agents are well known to those skilled in the cosmetic and pharmaceutical arts. Exemplary useful thickening agents include modified cellulose derivatives, natural gums, inorganic gel-forming mineral silicates, natural polymers and synthetically-made organic polymers.

In preferred practice, the thickening agent is water-swellable and capable of providing a viscosity measured in centipoise of at least about 1000, more preferably about 10,000 or more, as expressed for a 2 weight percent aqueous solution measured at about 20 degrees C. (about 68 degrees F.) with a Brookfield rotating viscometer.

One group of preferred thickening agents includes cellulosic thickeners, such as a water-swellable alkyl and hydroxyalkyl substituted polysaccharides having 1 to about 5 carbon atoms in the alkyl substituent. For example, the alkyl substituent can be selected from the group consisting of methyl and ethyl, and the hydroxyalkyl substituent can be selected from the group consisting of 2-hydroxyethyl, 2-hydroxypropyl and 2-hydroxybutyl. Particularly preferred is a hydroxypropyl cellulose thickener.

Several of these preferred cellulosic thickeners are available commercially. Particularly preferred among these thickeners are the cellulose ether derivatives available with varying degrees of polymerizations and with various substituent groups sold under the trademark METHOCEL by the Dow Chemical Company (Midland, Mich.).

Another preferred thickener is commonly called carbomer, which denotes a poly(acrylic acid) crosslinked with allyl ethers of pentaerythritol or allyl ethers of sucrose. Carbomer resins are commercially available under the trademark CARBOPOL from B.F. Goodrich Company (Cleveland, Ohio).

A description of the properties of various polymers and thickeners suitable for cosmetics generally, nail-care cosmetics and other personal-care products can be found in the "Polymers and Thickeners" documentary issue of *Cosmet. Toilet.*, 103, No. 12 (1988).

Those skilled in the cosmetic arts can readily determine the amount of thickener needed to achieve the viscosity desired. The selection of the thickener can be readily determined on the basis of convenience in handling, cost and type of rheology desired. While typically less than about 5 weight percent thickener is sufficient, the actual amount used depends upon the desired product consistency as is well-known in the formulation of viscous cosmetic products.

In practicing the composition of this invention, one or more cosmetic adjuvants which are well known in the cosmetic arts can be included for their generally recognized purposes. Particularly preferred are tissue-soothing agents, auxiliary emollients, emulsifiers, lubricants, preservatives and fragrance to augment the desirable cosmetic characteristic of the composition. It is understood that certain cosmetic ingredients can perform one or more of the above functions.

For example, tissue-soothing agents include plant-derived cosmetic ingredients, such as aloe, allantoin, gelatin and the like. Exemplary emollients can include squalene, hydrolyzed protein derivatives and the like. Emulsifiers where present are preferably substantially non-foaming, such cationic, nonionic or amphoteric surface active agents. Preferably, emulsifiers are used in amounts that do not interfere with the reconditioning agent of the auxiliary keratin-strengthening agent and which do not irritate the skin. Such emulsifiers can also include cationic polymers.

Exemplary lubricants can include liquid hydrocarbons, such as mineral oil and polybutenes, liquid waxes, such as jojoba oil and liquid cosmetic silicones. For purposes of prolonging the useful shelf-storage of a composition of this invention and of protecting against microbial contamination, a preservative, is preferably included. Useful preservatives include methyl paraben, propylparaben, 1,3-dimethylol-5,5-dimethylhydantoin, and the like. For purposes of increasing aesthetic appeal, a preferred composition includes a fragrance.

The foregoing cosmetic adjuvants have been listed by way of example and are not intended to limit the present invention in any way.

In one aspect, the extent of keratin hardening and strengthening achieved by practicing the principles of this invention can be determined by applying pressure to the free nail plate against the nail edge and measuring changes in nail flexion. Pressure is applied against the nail edge in a direction perpendicular to the long axis of the finger and towards the nail bed.

For example, the linear degree and extent of flexion of the free nail edge in response to a pressure of up to at least about 500 grams or more can be evaluated. For this purpose a pressure gauge having a means for registering the amount of pressure applied, preferably expressed in terms of grams, can be used. The degree of flexion curvature in millimeters flex from the planar axis can be measured. A useful commercially available gauge for this purpose which includes a plate against which the free nail edge can be positioned and is capable of registering the pressure applied thereto is a Chattillon Dial Tension Gauge, Model Ag-500 (Master Gauge Co., Chicago, Ill.).

A hardness and strength value can be assigned to describe the degree and flexion criteria using a scale of zero to five. A value of zero denotes complete nail flexion having substantially no resistance to pressure so that a straight-cross nail bend occurs under an applied pressure of less than about 250 grams. A value of 5 denotes substantially stable nail flexion having nearly total resistance to bending so that a curvature flex of about 1 millimeter or less occurs under an applied pressure of at least about 500 grams. The term "flexion" is used herein to denote the act of flexing or bending of the free edge of the nail.

In another aspect, the extent of keratin hardening and strengthening achieved with fluoride ion can be determined subjectively based on the subject's familiarity with their own historical pattern or unique pathology.

In another aspect, the extent of keratin hardening and strengthening achieved with fluoride ion can be evaluated by microscopically examining the appearance or character of the cellular structure of the nail keratin before and after practicing the method of this invention to observe changes associated with discernible keratin hardening and strengthening. For example, when nail keratin was viewed under magnification, a change in the imaging of the cellular structure was observed after practicing fluoride ion hardening and strengthening according to the principles of this invention. The nature of this changed image was not completely understood, except that it was associated with physically discernible keratin hardening and strengthening of the nails. Nails that were hardened and strengthened were free of any visible change in appearance but were smooth to the touch.

It is recognized that many other criteria and techniques can be used to measure hardening and strengthening of nail keratin. Thus, the above criteria and techniques are offered by way of example and are not limited thereto.

A keratin hardening and strengthening composition of this invention can be packaged in a suitable container, preferably a flexible plastic dispenser appropriately fitted with a means for dispensing the product directly onto the nail. This dispenser can comprise a flexible plastic bottle having a dispensing closure so that a ribbon or bead of the product can be squeezed directly onto the nail. Alternatively, the container can be fitted with an applicator brush or spatula and applied in the same manner as nail polishes. An amount of product about the size of a pea or large bead is preferably applied to each nail, so the choice of the container can be readily determined.

Where the composition is incorporated as part of a nail-care regimen, a kit containing an aqueous fluoride ion-containing composition embodying the principles of this invention is preferably included as at least one of the components. The other components can include one or more means for grooming the nails, such as manicuring implements; e.g., a nail file, buffing means, and nail-care cosmetics including nail polish and related accessories.

The following Examples illustrate the compositions and methods of this invention with generally preferred ingredients, but are not intended to be limited thereby.

EXAMPLE 1

This example illustrates several aqueous keratin hardening and strengthening compositions embodying the principles of this invention containing sodium fluoride as the active primary hardening and strengthening agent, lecithin or glycerin or combinations of each as the auxiliary keratin-strengthening agent and a cellulosic gum thickening agent.

| Ingredient | Percent By Weight | | | | | |
|---|---|---|---|---|---|---|
| | A | B | C | D | E | F |
| Sodium fluoride | 2 | 2 | 2 | 4 | 3 | 3 |
| Glycerin | 1.5 | — | 1 | 2 | 1 | 1.5 |
| Lecithin | — | 1.5 | 0.5 | 1 | 1 | — |
| Cellulosic thickener (Note a) | 2.5 | 2 | 3 | 3.5 | 3 | 3 |
| Preservative | Q.S. | Q.S. | Q.S. | Q.S. | Q.S. | Q.S. |
| Fragrance | Q.S. | Q.S. | Q.S. | Q.S. | Q.S. | Q.S. |
| Water to 100 percent | Q.S. | Q.S. | Q.S. | Q.S. | Q.S. | Q.S. |

Note a: Hydroxypropylmethyl cellulose sold as a series of polymers under the trademark METHOCEL by the Dow Chemical Company capable of producing a viscosity of between about 4,000 and 100,000 centipoise expressed as a 2 weight aqueous solution measured at about 20 degrees C. (about 68 degrees F.).

The compositions can be prepared by dispersing the thickener in a portion of the water, dissolving the remaining ingredients in the balance of the water and then combining the two solutions with agitating mixing to form a smooth viscous gel. Alternatively, the cellulosic thickener can be dispersed in one or both of the water-miscible ingredients, glycerin and lecithin and then mixed with the water solution containing the remainder of the ingredients. The pH of the composition can be adjusted, if necessary, to a pH of about 4 to about 7, preferably about 5 to about 6 with added acid.

The compositions can be packaged in small flexible plastic bottles fitted with dispensing closure so that a ribbon or large droplet of composition can be dispensed on squeezing the bottle.

EXAMPLE 2

This example illustrates the inclusion of a tissue-soothing agent derived from aloe in the composition of Example 1.

Aloe can be included by preparing an aqueous concentrate containing about 1 weight percent aloe prepared from powdered aloe and then adding about 1 weight percent of the aloe concentrate to the composition in place of a corresponding portion of water. Alternatively, a portion or all of the water content can be replaced by aloe vera mucilaginous gel obtained as the juice expressed from the leaves of the aloe barbadensis Miller plant.

For example, a composition corresponding to formula C of Example 1 to which aloe is added in this manner (identified as formula G) can provide a translucent, faintly yellow thixotropic gel that feels smooth to the touch and does not drip when it is applied to a watch glass or a finger nail even when the coated surface is held vertically or upside down.

EXAMPLE 3

This example illustrates the method of hardening and strengthening nail keratin with a preferred fluoride-ion containing aqueous composition.

The finger nails on the hands of a human volunteer are washed and dried to ensure that the surface of the nail is clean. Formula G of Example 2 is dispensed directly onto the surface of a fingernail and spread uniformly over the body of the nail to contact and coat all exposed surfaces, including the cuticle, the dorsal zone and the free edge. The amount applied is a sufficiently thick coating capable of maintaining the applied composition in moist contact with all surfaces for a period of at least about 5 to about 10 minutes. Additional amounts of composition can be applied, if desired, during the time period, to avoid drying-out of the composition. The same procedure is repeated for each fingernail by adjusting the amount of the composition dispensed accordingly. Typically, an amount about the size of a pea or large bead is sufficient.

After a hardening and strengthening period of at least about 5 minutes, the excess residual composition on the nail is removed by washing the nails with water. Alternatively, the excess composition can be wiped off with a tissue beforehand. If desired, washing can include soap and water.

The composition is easy to apply and distribute, is non-irritating to the skin and leaves the nails smooth to the touch.

The procedure can be repeated at least once daily for a period of at least about one week or until the desired hardness and strengthening is achieved.

EXAMPLE 4

This example illustrates the use of a synthetically-made organic polymer thickening agent in the procedure and compositions of Example 1.

| Ingredient | Percent By Weight | | | | | |
|---|---|---|---|---|---|---|
| | A | B | C | D | E | F |
| Sodium fluoride | 2 | 2 | 2 | 4 | 3 | 3 |
| Glycerin | 1.5 | — | 1 | 2 | 1 | 1.5 |
| Lecithin | — | 1.5 | 0.5 | 1 | 1 | — |
| Carbomer (Note b) | 1 | 2 | 2 | 4 | 3 | 3 |
| Preservative | Q.S. | Q.S. | Q.S. | Q.S. | Q.S. | Q.S. |
| Fragrance | Q.S. | Q.S. | Q.S. | Q.S. | Q.S. | Q.S. |
| Water to 100 percent | Q.S. | Q.S. | Q.S. | Q.S. | Q.S. | Q.S. |

Note b: Polymer of acrylic acid cross-linked with an allyl ether of pentaerythritol available as a series of polymers under the trademark CARBOPOL by B. F. Goodrich Company capable of producing a viscosity ranging from thick liquid syrups to gels.

The compositions can be prepared by dispersing the thickener in a portion of the water, dissolving the remaining ingredients in the balance of the water and then combining the two solutions with agitating mixing to form a smooth viscous gel. The viscosity of the compositions can be varied at a pH of about 3.5 to about 8 by either thickening the composition without neutralizing the carbomer or by neutralizing the carbomer to a pH above about 6 to about 8 with added base.

The compositions can be packaged in small flexible plastic bottles fitted with dispensing closure so that a ribbon or large droplet of composition can be dispensed on squeezing the bottle.

EXAMPLE 5

The procedure of Example 3 is followed, except that after removing the composition, nail polish is applied. The polish film can adhere normally. Thereafter, the composition can be applied only to the exposed keratinous surface of the cuticle and to the nail edge. Hardening and strengthening effectively keeps the nail tips from splitting and helps maintain normal nail hardness and strength during outgrowth of the nail without adversely affecting the user's normal nail-care regimen.

EXAMPLE 6

This example illustrates the hardening and strengthening of nail keratin based on measuring the flexion of the free nail edge under applied pressure of up to at least about 500 grams, using a Chattillon dial tension gauge, Model AG-500.

For this purpose, a human volunteer having a free nail edge of at least about 4 to about 5 millimeters is selected. The initial hardness and strength of the volunteer's nail is determined by placing the subject's hand in a stationary position on a flat surface, and then grasping a selected test finger at the first knuckle to hold it stable. The plate of the Chattillon dial tension gauge is placed against the free nail edge of the stabilized finger and pressure is applied towards the nail bed. A pressure of up to at least about 500 grams is applied to that nail tip in the direction perpendicular to the long axis of the finger and toward the nail bed. The grams pressure is recorded. The deflexion and amount of curving flex of the nail tip from the planar surface, respectfully, can be visually estimated or actually measured in millimeters at a given registered applied pressure. A value can be assigned according to the following Hardness and Strength scale.

| Value | Flexion Criteria for Nail Edge |
|---|---|
| 0 | complete flexion; substantially no resistance to pressure; straight across nail bend or curve of about 4 to about 5 millimeters flex seen under an applied pressure of less than about 250 grams. |
| 1 | nearly complete flexion; slight resistance to pressure; straight across nail bend or curve of about 3 to about 4 millimeters seen under an applied pressure of less than about 350 grams |
| 2 | moderate flexion; moderate moisture; curves of about 3 and 4 millimeters flex under an applied pressure of less than about 500 grams |
| 3 | slight flexion; firm resistance; curves evenly into body of nail base about 2 to about 3 millimeters flex under an applied pressure of less than about 500 grams |
| 4 | very slight flexion; strength resistance; curves slightly about 1 to about 2 millimeters flex under an applied pressure of less than about 500 grams |
| 5 | stable flexion; substantially total resistance; curve flex is about 1 millimeter or less under applied pressure of at least about 500 grams |

By having the volunteer practice the composition and method of Example 3, the extent of hardening and strengthening can be re-measured as above. The same procedure can be repeated for each fingernail of the hands of the same volunteer. Repeat application by the procedure of Example 3 at least once daily can be practiced until the desired level of hardness and strength is achieved.

The following data illustrate average hardening and strengthening values that can be obtained when the composition and procedure of Example 3 is practiced. The data is based on an average of three measurements taken for the weakest fingernail on either hand using the ring finger (R) or the middle finger (M) as the selected test finger of ten healthy female volunteers.

| | Hardness and Strength Value (V) For Flexion in Millimeters (M) at Applied Gram Pressure (G) After a Once-Daily Regimen | | | | |
|---|---|---|---|---|---|
| Volunteer | At Start | At Week 2 | At Week 4 | At Week 8 | At Week 12 |
| A (R) V | 1 | 2 | 3 | 4 | 5 |
| M | 3 | 3 | 2 | 2 | 1 |
| G | 200 | 350 | 350 | 500 | 430 |
| B (R) V | 1 | 2 | 3 | 4 | 5 |
| M | 3 | 3 | 2 | 2 | 1 |
| G | 250 | 350 | 320 | 490 | 480 |
| C (M) V | 0 | 2 | 3 | 4 | 4 |
| M | 4 | 3 | 3 | 2 | 1 |
| G | 200 | 300 | 400 | 400 | 350 |
| D (R) V | 1 | 2 | 3 | 5 | 5 |
| M | 3 | 3 | 2 | 1 | 1 |
| G | 250 | 350 | 450 | 400 | 500 |
| E (M) V | 1 | 2 | 3 | 4 | 5 |
| M | 3 | 3 | 2 | 1 | 1 |
| G | 250 | 375 | 400 | 380 | 470 |
| F (R) V | 1 | 2 | 3 | 5 | 5 |
| M | 3 | 3 | 2 | 1 | 1 |
| G | 300 | 400 | 370 | 480 | 500 |
| G (R) V | 1 | 2 | 3 | 5 | 5 |
| M | 3 | 3 | 2 | 1 | 1 |
| G | 250 | 375 | 400 | 420 | 500 |
| H (M) V | 1 | 2 | 3 | 4 | 5 |
| M | 3 | 3 | 2 | 2 | 1 |
| G | 350 | 475 | 400 | 500 | 480 |
| I (R) V | 1 | 2 | 3 | 5 | 5 |
| M | 3 | 3 | 2 | 1 | 1 |
| G | 350 | 480 | 400 | 420 | 490 |
| J (M) V | 1 | 2 | 3 | 4 | 5 |
| M | 3 | 3 | 2 | 2 | 1 |
| G | 350 | 450 | 375 | 480 | 420 |

Except for some variation seen in the individual measures for flexion and in gram pressure recorded, the average value data overall shows a measurable increase in hardness and strength from a nail-care regimen of at least once-daily repeated applications. It is recognized that some variation between the hardness and strength of each of the nails of the hand and between hands as well is normally expected.

No color change or discoloration is seen in nails following such a regimen and the surface of the hardened and strengthened nail feels smooth to the touch.

The present invention has been described generally and with respect the preferred embodiments. It will be understood that modifications and variations of the disclosed method and compositions may be made without departing from the spirit and scope of the novel concept of the present invention.

What is claimed:

1. A method of hardening and strengthening a keratinized appendage of a mammal, the method comprising the steps of:

(a) providing an aqueous keratin hardening and strengthening composition including an effective amount of a fluoride ion, the composition having a pH of about 3.5 to about 8;
(b) applying the composition topically to coat the keratinized appendage with an amount sufficient to substantially contact all exposed surfaces thereof;
(c) maintaining the composition in such contact in a substantially moist state for at least about one minute;
(d) removing excess composition; and
(e) repeating steps (a)–(d) at least once daily or until the desired hardness and strength is obtained.

2. The method of claim 1 wherein the fluoride ion in the composition is from a fluoride compound selected from the group consisting of water-soluble fluoride salts, and water-soluble complex fluoride salts, used alone or in combination.

3. The method of claim 2 wherein the fluoride compound in the composition includes a cation selected from the group consisting of aluminum, ammonium, sodium, potassium and tin.

4. The method of claim 3 wherein the fluoride compound in the composition is selected from the group consisting of aluminum fluoride, sodium fluoride, potassium fluoride, stannous fluoride, ammonium hexafluorophosphate, sodium monofluorophosphate, stannous fluorozirconate, stannous chlorofluoride, and stannous monofluorophospate, used alone or in combination.

5. The method of claim 1 wherein the composition includes an auxiliary keratin-strengthening agent comprising at least one reconditioner selected from the group consisting of lipids and polyols, used alone or in combination.

6. The method of claim 5 wherein the auxiliary keratin-strengthening agent is a lipid selected from the group consisting of neutral fats, fatty acids having about 12 or more carbon atoms, phospholipids, sterols, lipoproteins, and derivatives of each.

7. The method of claim 6 wherein the lipid is a phospholipid selected from the group consisting of lecithin and derivatives of lecithin.

8. The method of claim 5 wherein the auxiliary keratin-strengthening agent is a polyol member from the group consisting of polyhydric aliphatic alcohols having at least three or more carbon atoms in the aliphatic chain and at least two or more hydroxyl groups.

9. The method of claim 8 wherein the polyol is glycerin.

10. An aqueous composition for hardening and strengthening a keratinized appendage of a mammal comprising a cosmetically-acceptable aqueous vehicle having dissolved therein a physiologically tolerable keratin hardening and strengthening agent including an effective amount of fluoride ion, the composition having a pH of about 3.5 to about 8.

11. The composition of claim 10 wherein the fluoride ion is from a fluoride compound selected from the group consisting of water-soluble fluoride salts, and water-soluble complex fluoride salts, used alone or in combination.

12. The composition of claim 11 wherein the fluoride compound includes a cation selected from the group consisting of aluminum, ammonium, sodium, potassium and tin.

13. The composition of claim 12 wherein the fluoride compound is selected from the group consisting of aluminum fluoride, sodium fluoride, potassium fluoride, stannous fluoride, ammonium hexafluorophosphate, sodium monofluorophosphate, stannous fluorozirconate, stannous chlorofluoride, and stannous monofluorophosphate, used alone or in combination.

14. The composition of claim 10 wherein the amount of fluoride ion is present at a concentration of at least about 500 parts per million.

15. The composition of claim 10 wherein the composition includes an auxiliary keratin-strengthening agent comprising at least one reconditioner selected from the group consisting of lipids and polyols, used alone or in combination.

16. The composition of claim 15 wherein the auxiliary keratin-strengthening agent is a lipid selected from the group consisting of substantially neutral fats, long chain fatty acids having about 12 or more carbon atoms, phospholipids, sterols, lipoproteins, and derivatives of each, used alone or in combination.

17. The composition of claim 15 wherein the auxiliary keratin-strengthening agent is a polyol selected from the group consisting of polyhydric aliphatic alcohols having at least three or more carbon atoms in the aliphatic chain and at least two or more hydroxyl groups.

18. The composition of claim 10 wherein the composition includes a thickening agent present in an amount sufficient to maintain the composition in contact with the keratin for at least one minute.

19. The composition of claim 18 wherein the thickening agent is a water-swellable thickener selected from the group consisting of cellulose derivatives, natural gums, inorganic gel-forming mineral silicates, natural polymers, and synthetically-made organic polymers.

20. The composition of claim 18 wherein the thickening agent is a cellulosic thickener selected from the group consisting of water-swellable alkyl and hydroxylalkyl substituted polysaccharide having one to about five carbon atoms in the alkyl substituent.

21. The composition of claim 18 wherein the thickening agent is a synthetically-made organic polymer selected from the group consisting of poly(acrylic acid) cross-linked with allyl ethers of pentaerythritol or allyl ethers of sucrose.

22. The composition of claim 10 wherein the composition includes a reconditioning amount of auxiliary keratin-strengthening agents comprising a phospholipid selected from the group consisting of lecithin and derivatives of lecithin and a polyol.

23. The composition of claim 22 wherein the polyol is selected from the group consisting of glycerine, propylene glycol, butylene glycol, hexylene glycol and sugar alcohols having the general formula $CH_2OH(CHOH)_nCH_2OH$ where n may be from 2 to 5, used alone or in combination.

24. The composition of claim 23 wherein the composition further includes a thickening agent.

25. The composition of claim 24 wherein the thickening agent is a cellulosic thickener.

26. The composition of claim 10 wherein the pH of the composition is about 4 to about 7.

27. The composition of claim 10 wherein the fluoride ion is from at least one alkali metal fluoride compound.

28. The composition of claim 27 wherein the fluoride compound is sodium fluoride present at about 1 percent to about 6 percent.

29. The composition of claim 10 further including one or more cosmetic adjuvants selected from the group consisting of tissue-soothing agents, emollients, lubricants, preservatives, and fragrance.

30. An aqueous cosmetic keratin hardening and strengthening composition for the nails of living humans including an effective amount of a fluoride ion from sodium fluoride present at about 1 to about 6 weight percent, an effective reconditioning amount of auxiliary keratin-strengthening agent comprising lecithin and glycerine in combination, the total amount of the combination present being no greater than about 5 weight percent, and an effective amount of thickening agent, the composition having a pH of about 4 to about 7.

31. The composition of claim 30 further including one or more cosmetic adjuvants selected from the group consisting of tissue-soothing agents, emollients, emulsifiers, lubricants, preservatives, and fragrance.

32. The composition of claim 31 in the form of a gel.

33. A method of hardening and strengthening the nails of humans comprising the steps of:
   (a) providing the aqueous composition of claim 31;
   (b) applying the composition topically to contact and coat all exposed surfaces of the nail;
   (c) maintaining the composition in such contact in a moist state for at least about five minutes;
   (d) removing excess composition; and
   (e) repeating steps (a)-(d) at least once daily or until the desired hardness and strength is obtained.

34. A method of hardening and strengthening the keratin of a mammal comprising the step of:
   (a) providing the aqueous composition of claim 10,
   (b) applying the composition topically to contact and coat all exposed surfaces of the keratin;
   (c) maintaining the composition in such contact in a substantially moist state for at least about one minute;
   (d) removing excess composition; and
   (e) repeating steps (a)-(d) at least once daily or until the desired hardness and strength is obtained.

35. A kit containing one or more means for grooming nails including the nail hardening and strengthening composition of claim 10.

* * * * *

UNITED STATES PATENT AND TRADEMARK OFFICE
CERTIFICATE OF CORRECTION

PATENT NO. : 4,919,920

DATED : April 24, 1990

INVENTOR(S) : John B. Devos

It is certified that error appears in the above-identified patent and that said Letters Patent is hereby corrected as shown below:

Column 15, line 29, claim 4, "monofluorophospate" should read --monofluorophosphate--.

Column 18, line 10, claim 34, "," should read --;--.

Signed and Sealed this

First Day of October, 1991

Attest:

Attesting Officer

HARRY F. MANBECK, JR.

Commissioner of Patents and Trademarks